United States Patent [19]
Schneider et al.

[11] Patent Number: 6,013,273
[45] Date of Patent: Jan. 11, 2000

[54] TREATMENT OF ENDOTOXIC SHOCK

[75] Inventors: Heinz Schneider, Cordast, Switzerland; Ronald G. Thurman, Chapel Hill, N.C.

[73] Assignee: Novartis Nutrition AG, Berne, Switzerland

[21] Appl. No.: 08/789,773

[22] Filed: Jan. 27, 1997

[51] Int. Cl.$^7$ ........................................... A61K 9/68
[52] U.S. Cl. ........................................... 424/440; 514/893
[58] Field of Search ........................... 424/440; 564/293; 514/893

[56] References Cited

U.S. PATENT DOCUMENTS 5,374,651  12/1994  Kilbourn et al. ................. 514/400

FOREIGN PATENT DOCUMENTS

| 0 001 924 | 5/1979 | European Pat. Off. | ..... A61K 31/495 |
| 0 217 258 | 4/1987 | European Pat. Off. | ....... A61K 31/14 |
| 0 324 227 | 7/1989 | European Pat. Off. | .................. 37/18 |
| 94 03181 | 2/1994 | WIPO | ......................... A61K 31/685 |

OTHER PUBLICATIONS

Malone et al., *Excerpta Medica* (EMBASE), #94077814, 1995.
Altura BM, et al. (1966). "Influence of Choline on the Reticuloendothelial System and on Survival after Experimental Shock", vol. 3, No. 1, p. 57–64.
List PH, et al. (1972). "Hagers Hanbuch Der Pharmazeutischen Praxis, 4th D., vol. 3" p. 885–890. (*Copies not provided.).
Malone M, et al., (1994). "Long–term Hyperalimentation", Curr Opin Gastroenterol, vol. 10, No. 2, p. 227–234.
Reichard SM, (1972). "RES Stimulation and Transfer of Protection Against Shock", vol. 12, No. 6.
Reynolds JEF, (1996). "Martindale the Extra Pharmacopoeia" p. 1356–1357.
Lieber et al., Phosphatidylcholine Protects Against Fibrosis and Cirrhosis in the Baboon, Gastroenterology 1994; 106:152–159.
Bread et al., Triglyceride–rich Lipoproteins Prevent Septic Death in Rats, 1995 vol. 182 pp. 1–1066.
Harris et al., Human Very Low Density Lipoproteins and Chylomicrons can Protect Against Endotoxin–induced Death in Mice, vol. 86, Sep. 1990, 696–702.
Feingold et al., Role for Circulating Lipoproteins in Protection from Endotoxin Toxicity, vol. 63, No. 5, Infection and Immunity, May 1995, p. 2041–2046.
Ikejima et al., A diet containing glycine improves survival in Endotoxin shock in the rat, 1996, vol. 271 No. 1, Part 1, pp. G97–G103.

*Primary Examiner*—Thurman K. Page
*Assistant Examiner*—D. Faulkner
*Attorney, Agent, or Firm*—Michael P. Morris

[57] ABSTRACT

The invention provides a method for the treatment of endotoxic shock comprising administering to a human or other mammal in need of such a treatment an effective amount of choline for reducing endotoxin-induced injury and mortality and a nutritional composition comprising choline, whereby the composition provides a daily dosage of at least 1.5 g choline, the upper limit being 20 g of choline per day.

6 Claims, 7 Drawing Sheets

TREATMENT OF ENDOTOXIC SHOCK

The present invention relates to the reduction of endotoxin-induced injury and mortality.

Gram-negative bacterial infection involves the release of massive amounts of endotoxin into the systemic circulation. Endotoxins (lipopolysaccharides) are a cell wall component of gram-negative bacteria and are cleared from the systemic circulation largely by Kupffer cells, the resident macrophage of the liver. Phagocytosis of endotoxin activates Kupffer cells to release prostaglandins, cytokines and free radicals that lead to hypermetabolism and cause liver injury. The release of endotoxin and Kupffer cell activation are also important events in the genesis of alcoholic liver disease. It is further well known that LPS (lipopolysaccharides) and TNF-$\alpha$ increase circulating VLDL (very low density lipoprotein), a lipoprotein that can bind and detoxify endotoxin.

Sepsis or endotoxic shock is a major health problem which occurs not infrequently following major surgery and trauma and often leads to refractory hypotension and multiple organ failure. There are many deaths from these conditions annually which represent a unique challenge in critical care medicine.

It has now surprisingly been found that choline reduces endotoxin-induced injury and mortality and thereby protects against endotoxic shock and its consequences.

The present examples demonstrate the effectiveness of choline in the prevention of mortality in a rat model of endotoxin shock. In addition, choline also prevented liver and lung injury. Previously, it has been shown that dietary supplementation with glycine blocks endotoxin-induced injury and subsequent mortality. In this study, feeding a diet rich in both glycine and choline was surprisingly even more effective in preventing mortality, suggesting that choline and glycine act via different mechanisms. Hence, the examples clearly demonstrate the effectiveness of choline in preventing endotoxin-induced injury and mortality and suggest that choline also prevents endotoxin-related injuries such as alcoholic liver injury.

The present invention accordingly provides the use of choline in the preparation of a medicament or nutritional formulation for the reduction and/or prevention of endotoxin-induced injury and mortality.

Further the invention provides a method for the treatment of endotoxic shock comprising administering to a human or other mammal in need of such a treatment an effective amount of choline for reducing endotoxin-induced injury and mortality.

For use in the compositions, formulations, diets and methods of the invention, choline is conveniently employed as a free base, in physiologically acceptable salt form, in form of lecithin, and/or in form of natural sources rich in lecithin or choline such as egg yolk, kidney, liver, heart, seeds, vegetables, and legumes. Preferably choline is employed as choline tartrate.

An "effective amount of choline" as used herein lies typically in the range of 1.5 to 20 g, preferably 3 to 14 g, more preferred 6 to 10 g of the free base per 24 hours. The person skilled in the art will know how to adjust the dosage if other sources than the free base of choline are used. If e.g. lecithin is used the amount by weight of lecithin used will roughly be five times the amount of free base of choline. The amount of choline to be administered depends to a large extent on the patient's specific requirements. Such daily amounts of choline are suitable for treatment of the desired effects as well as for prophylactic/pretreatment.

The invention also provides for the use of a mixture of glycine and choline in the preparation of a medicament or nutritional formulation for the reduction and/or prevention of endotoxin-induced injury and mortality.

Also provided is a method for the treatment of endotoxic shock comprising administering to a human or other mammal in need of such a treatment a combined amount of choline and glycine effective for reducing endotoxin-induced injury and mortality.

For use in the compositions, formulations, diets and methods of the invention, glycine is conveniently employed in the form of the free base of the amino acid, in the form of glycine precursors, in particular alanine or serine, likewise in free amino acid base form, in physiologically acceptable salt form of said amino acids, or in form of mixtures of said amino acids and/or physiologically acceptable salts thereof. Glycine is preferably used in form of the free base of the amino acid, in physiologically acceptable salt form or in the form of a mixture of glycine in free amino acid base form with glycine in physiologically acceptable salt form; most preferably glycine is in free amino acid base form. Glycine may also be used in the form of dipeptides according to the invention.

An "effective amount of glycine" as used herein lies typically in the range of 1.5 to 75 g, preferably 2 to 60 g, particularly preferred 20 to 40 g of the free base of the amino acid per 24 hours. The person skilled in the art will know how to adjust the dosage if other sources than the free base of glycine are used. The amount glycine to be administered depends to a large extent on the patient's specific requirements. Such daily amounts of glycine are suitable for treatment of the desired effects as well as for prophylactic/pretreatment.

Typically the ratio of choline:glycine is from 1:1 to 1:50, preferably 1:5 to 1:20, particularly preferred from 1:7 to 1:15. The ratio given is with respect to the free base of choline and glycine the person skilled in the art will know how to adjust the ratios if other sources of choline and glycine are used.

The invention further provides the use of choline in the preparation of a medicament or nutritional formulation for reducing and/or preventing endotoxin-related injuries such as alcoholic liver injury.

Still further provided is a method for the treatment of endotoxin-related injury comprising administering to a human or other mammal in need of such a treatment an effective amount of choline to reduce the endotoxin-related injury such as alcoholic liver injury.

Further provided is a nutritional composition comprising choline, whereby the composition provides a daily dosage of at least 1.5 g choline, the upper limit being 20 g of choline per day.

Also provided is a nutritional composition comprising:
 1.5 to 20 parts of choline and
 1.5 to 75 parts of glycine,
whereby the composition provides a daily dosage of at least 1.5 g to at the most 20 g of choline and of at least 1.5 g to at the most 75 g of glycine.

The nutritional formulation or medicament may be administered either prophylactically, e.g. preoperatively, in the acute phase, e.g. postoperatively, or both.

The nutritional formulation or medicament may be administered to the patient enterally or parenterally. The enteral administration route is preferred, particularly for subsequent or prophylactic treatment; particularly contemplated enteral administration routes are oral administration and/or tube feeding. The medicament or formulation is conveniently administered in the form of an aqueous liquid. The medicament or formulation in a form suitable for enteral application is accordingly preferably aqueous or in powder form, whereby the powder is conveniently added to water prior to use. For use in tube feeding, the amount of water to be added will depend, inter alict, on the patient's fluid requirements and condition. It will be appreciated that, for acute treatment, the parenteral application route may be preferred.

Generally, it is indicated to use choline in combination with one or more of the following components:

(i) glycine;

(ii) omega-3 polyunsaturated fatty acids (PUFAs) where desired in admixture with omega-6 PUFAs;

(iii) L-arginine or other physiologically acceptable compounds associated with the synthesis of polyamines, or mixtures thereof; and (iv) a nucleobase source.

Nucleobase sources suitable for use in combination with the amino acids of the invention comprise or consist of natural nucleobases, nucleosides, nucleotides, RNA, DNA, equivalents thereof and/of mixtures comprising one or more of these compounds.

Natural nucleobases include the purines adenine and guanine as well as the pyrimidines cytosine, thymine and uracil. Where the nucleobase source is in the form of free nucleobases, it is preferably uracil.

Natural nucleosides include the ribose nucleosides adenosine, guanosine, uridine and cytidine and the deoxyribose nucleosides deoxyadenosine, deoxyguanosine, deoxythymidine and deoxycytidine.

Natural nucleotides include phosphate esters of natural nucleosides, such as the monophosphates adenylate (AMP), guanylate (GMP), uridylate (UMP), cytidylate (CMP), deoxythymidiylate (dTMP), deoxycytidylate (dCMP), and diphosphates and triphosphates of natural nucleosides such as ADP and ATP.

A purified nucleobase source, such as yeast is preferred. However, other sources such as meat and the like may be used. Preferably the nucleobase source is RNA. Accordingly, the invention provides medicaments or nutritional formulations comprising effective amounts of:

(a) choline (component (a)) in association with one or more components selected from (b) glycine (component (b));

(c) omega-3 PUFAs where desired in admixture with omega-6 PUFAs (component (c));

(d) L-arginine or other physiologically acceptable compounds associated with the synthesis of polyamines, or mixtures thereof (component (d)); and (e) a nucleobase source (component (e)).

Said medicaments and nutritional formulations are hereinafter designated "diets of the inventions".

One unit dose of such a medicament or nutritional formulation preferably comprises 1.5 to 20 parts by weight of component (a) in association with the following amounts of one or more components selected from (b) to (e): 1.5 to 75 parts by weight of component (b), 0.1 to 20 parts by weight of component (c), 3 to 40 parts by weight of component (d) and 0.1 to 4.0 parts by weight of component (e). Particularly preferred one unit dose comprises 1.5 to 20 parts by weight of component (a) in association with the following amounts of one or more components selected from (b) to (e): 2 to 60 parts by weight of component (b), 2 to 5 parts by weight of component (c), 7.5 to 20 parts by weight of component (d) and 1.7 to 2.0 parts by weight of component (e).

The amount of components (a) to (e) administered daily will conveniently correspond to 1.5 to 20 g for component (a), 1.5 to 75 g, preferably 2 to 60 g, particularly preferred 20 to 40 g for component (b), 0.1 to 20 g, preferably 2 to 5 g, for component (c), 3 to 40 g, preferably 7.5 to 20 g, for component (d) and 0.1 to 4.0 g, preferably 1.7 to 2.0 g, for component (e).

With respect to component (e) the above dosage is indicated for RNA, DNA, nucleosides or nucleotides. For nucleobases one weight unit of nucleobases is regarded to be equivalent to 2.5 to 3.0 weight units of RNA, DNA, nucleosides or nucleotides.

Where medicaments or nutritional formulations comprising choline in combination with one or more of the above-mentioned components (b) to (e) are used, such medicaments or nutritional formulations will conveniently comprise in one unit dose (a) 1.5 to 20 parts by weight of choline, in combination with one or more compounds selected from the group consisting of (b) 1.5 to 75 parts by weight glycine (c) 2 to 5 parts by weight omega-3 polyunsaturated fatty acids;

(d) 7.5 to 20 parts by weight L-arginine or L-ornithine, or mixtures thereof; and (e) 1.7 to 2.0 parts by weight RNA.

Preferred medicaments or nutritional formulations comprise in one unit dose:

(a) from 1.5 to 20 parts by weight of choline, in association with (b) 1.5 to 75 parts by weight, preferably 2 to 60 parts by weight, particularly preferred 20 to 40 parts by weight, of glycine.

Further preferred medicaments or nutritional formulations comprise in one unit dose:

(a) from 1.5 to 20 parts by weight choline, in association with omega-3 PUFAs which are conveniently protected against peroxidation.

Physiologically acceptable ways of protecting omega-3 PUFAs against peroxidation are known in the art. They include physiologically acceptable micro-encapsulation of omega-3 PUFAs and the use of physiologically acceptable antioxidants.

A typical example suitable for use as physiologically acceptable micro-encapsulation agents is starch. The micro-encapsulation can be effected in a manner known per sc. The micro-encapsulates may be coated in a manner known per se, by physiologically acceptable coating agents such as Gum Arabic.

Typical examples of antioxidants suitable for use in the method of the invention include antioxidant vitamins such as Vitamin C, Vitamin E or mixtures thereof.

The amount of antioxidant added should be sufficient to prevent peroxidation of the omega-3 PUFAs. Such amounts can be easily calculated. In general, for convenience, any antioxidants employed to prevent peroxidation, will be employed in excess. It will be appreciated that the presence of any other agent administered in association with the omega-3 PUFAs may require adjustment of the amount of antioxidant to be employed.

The omega-3 PUFAs may be employed in a form suitable for the physiological supply of omega-3 PUFAs, e.g. in free acid form, in triglyceride form, or in the form of physiologically acceptable natural sources of omega-3 PUFAs. Such natural sources include linseed oil and fish oils such as menhaden oil, salmon oil, mackerel oil, tuna oil, cod-liver oil and anchovy oil. Said natural sources, in particular, the fish oils, comprise substantial amounts of omega-3 fatty acids. Where the omega-3 PUFAs are employed in triglyceride form, said triglycerides may comprise esters with other physiologically acceptable fatty acids. Preferred omega-3 PUFAs include eicosapentaenoic acid (EPA) and docosahexaenoic acid (DHA), in free acid form, in triglyceride form or in form of natural sources having a high EPA and/or DHA content.

In general, favorable effects are obtained when administering the diets of the invention in the form of a formula diet, which may, depending on the circumstances be a complete formula diet (i.e., a diet supplying essentially all required energy, amino acids, vitamins, minerals and trace elements) or a diet supplement. The diet will conveniently be taken in aqueous liquid form. A formula diet accordingly may comprise a source of carbohydrates, lipids fat (fat source) and protein (nitrogen source), and choline as a free base, in physiologically acceptable salt form, in form of lecithin, and/or in form of natural sources rich in lecithin or choline such as egg yolk, kidney, liver, heart, seeds, vegetables, and legumes, characterized in that choline is present in the formula diet in an amount of about 0.15 to 3.3 g per 100 g (amount of choline in free base form). The formula diet will preferably further comprise other nutritionally advantageous components such as vitamins, minerals, trace elements, fibers (preferably soluble fibers).

Examples of suitable nitrogen sources include nutritionally acceptable proteins such as soy bean or whey derived proteins, caseinates, and/or protein hydrolysates. Suitable carbohydrate sources include sugars such as maltodextrins. Examples of suitable fat sources include triglycerides, as well as di- and monoglycerides.

Examples of vitamins suitable for incorporation into the medicament or formulation of the invention include Vitamin E, Vitamin A, Vitamin D, Vitamin K, folic acid, thiamin, riboflavin, Vitamin $B_1$, $B_2$, $B_6$ and $B_{12}$, niacin, biotin and panthotenic acid in nutritionally acceptable form.

Examples of mineral elements and trace elements suitable for incorporation into the medicament or formulation include sodium, potassium, calcium, phosphorous, magnesium, manganese, copper, zinc, iron, selenium, chromium, and molybdenum in nutritionally acceptable form.

In particular, the medicament or formulation will preferably comprise beta-carotene (Vitamin A), Vitamin E, Vitamin C, thiamine, Vitamin $B_{12}$, choline, selenium and zinc in nutritionally acceptable form.

The term "soluble fiber" as used herein refers to fibers which are able to undergo substantial fermentation in the colon ultimately to produce short chain fatty acids. Examples of suitable soluble fibers include pectin, guar gum, locust bean gum, xanthan gum which may optionally be hydrolysed. For adults, the total amount of soluble fibre per day will conveniently lie in the range of from 3 to 30 g.

It will be appreciated that omega-3 PUFAs may be administered in higher amounts than those indicated hereinabove, and that such higher amounts will in general not impair the desired effect or provoke undesired side effects.

Compounds particularly suitable for use as component (d) in the formulation of the invention include L-arginine and L-ornithine, most preferably L-arginine. Component (d) may be employed in free form, physiologically acceptable salt form, e.g. in the form of a salt with phosphoric acid, citric acid, tartaric acid, fumaric acid, adipic acid or lactic acid, or in small peptide form. Preferably L-arginine in free form is employed.

The term small peptides as used herein refers to peptides having from 2 to 6, preferably from 2 to 4 amino acids.

As already indicated, omega-3 PUFAs will conveniently be administered in the form of fish oils, protected or not against peroxidation. Such fish oils also comprises omega-6 PUFAs.

Omega-6 PUFAs have also a favorable effect on the immune response and on the resistance to infection upon surgery. Accordingly, diets of the invention may conveniently further comprise omega-6 PUFAs.

For the purpose of the invention the omega-6 PUFAs may be in free acid form or in a form suitable for the physiological supply of omega-6 PUFAs, e.g. in triglyceride form. Examples of omega-6 PUFAs particularly appropriate for use according to the invention, include linoleic acid and arachidonic acid, linoleic acid being most preferred. Examples of suitable omega-6 PUFA sources are known in the art. They include fish oils and vegetable oils. Examples of omega-6 PUFA sources having a high linoleic acid content are safflower oil, sunflower oil, soy oil, cotton oil and corn oil.

Administration of a daily amount of omega-6 PUFAs in the range of from 1.5 to 5.0 g will in general suffice to attain a favorable effect. One unit dose of the medicaments or nutritional formulation defined above may accordingly further contain 1.5 to 5 parts by weight of omega-6 PUFAs.

In addition to components (b) to (e), and omega-6 PUFAs further components may be added to the diets of the invention and may have a beneficial effect on the activity of the glycine. An example of such beneficial components are omega-9 PUFAs. A preferred natural source for such fatty acid mixtures are fish oils. For taste and other reasons, the fish oils will, in oral application forms, preferably be used in encapsulated form.

Where the formula diet of the invention is intended for use as a nutritional supplement (e.g., pre-operative treatment), the amount of energy supplied by it should not be too excessive, in order not to unnecessarily suppress the patients appetite. The supplement should conveniently comprise energy sources in an amount supplying from 600 to 1000 Kcal/day. For use as a complete formula diet (e.g., for post-operative treatment, treatment of trauma), the diets of the invention will conveniently supply from 600 to 1500 Kcal/day. The contribution of the nitrogen source, carbohydrate source and lipid source to the total daily caloric may vary within wide ranges. In preferred formulations of the invention the carbohydrate source provides for 40 to 70% of the total energy supply and, the nitrogen and fatty acid source each for 15 to 30% of the total energy supply of the formulation. For use as complete diet, the diet of the invention will conveniently be administered in aqueous liquid form in volumes in the range of from 500 ml to 3000 ml. For use as a supplement, the administration may be in powder or liquid form.

Patients who can benefit from the present invention include patients undergoing major surgery, burn patients, patients suffering from acute trauma and/or sepsis, patients with preeclampsia, patients with acute liver disease caused by alcohol or viral induced liver injury.

The diets of the invention are as already set out above particularly suitable for treatment of patients due for surgery. Such pretreatment will be most effective when administering the diet of the invention in the form of a supplement. The supplement will advantageously be administered over a period of 2 days or longer. In general, a pretreatment starting 1 to 6 days before surgery, and during said 1–6 day period will be sufficient to attain the desired effect.

The supplement will conveniently be administered in the form of unit doses suitable for administration of the supplement 3 to 4 times per day. Where the diets of the invention comprise energy sources, it is appropriate not to supply more than 1500 Kcal/day. Apart from this limitation with respect to the energy supply, diet supplements of the invention can and will conveniently be supplied in the form of complete formula diets as described above.

Typical administration forms suitable for such acute treatment are, e.g., the aqueous solutions disclosed hereinbelow.

Typical pharmacologically acceptable formulation forms for oral administration will further comprise pharmacologically acceptable diluents, carriers, vitamins, spices, pigments and/or other adjuvants well known to the skilled person to be suitable for incorporation into such formulation.

The diets and formulations of the invention may be obtained in a manner known per se, e.g., by admixing the ingredients.

Typical formulations suitable for use according to the invention containing choline and water include, e.g., aqueous solutions consisting essentially of 0.1% to 90% by weight of choline and 10% to 99.9% by weight of distilled water. Choline may be present in a concentrated form of the solution in an amount of from 15 to 90% (by weight of the solution). Concentrated solutions are suitable for dilution to application forms or for use in acute treatment. Application forms having a lower content (e.g. 0.1 to 5%) of choline will in general be indicated for prophylactic purposes; concentrated forms of the solution having a higher content (e.g. 5% to 40% by weight) choline will in general be more suitable for acute treatment.

Other formulations suitable for inclusion in the medicament or formulation of the invention, in particular for parenteral application, include infusion solutions such as Ringer's injection solution, lactated Ringer's injection solution, crystalloids, colloids or other plasma substitutes, in association or enriched with about 0.15 to 3.3 g per liter infusion solution of choline. Ringer's injection solution is a sterile solution, containing from 3.23 to 3.54 g of sodium (equivalent to from 8.2 to 9.0 g of sodium chloride), from 0.149 to 0.165 of potassium (equivalent to from 0.285 to 0.315 g of potassium chloride), from 0.082 to 0.098 g of calcium (equivalent to from 0.3 to 0.36 g of calcium chloride, in the form of $CaCl_2.2H_2O$), from 5.23 to 5.80 g of chloride (as NaCl, KCl and $CaCl_2.2H_2O$) and water in sufficient quantity to give 1000 ml solution. Lactated Ringer's Injection solution is a sterile solution containing from 2.85 g to 3.15 g sodium, as chloride and lactate), from 0.141 to 0.173 g of potassium (equivalent to from 0.27 g to 0.33 g of potassium chloride), from 0.049 to 0.060 g calcium (equivalent to from 0.18 g to 0.22 g of $CaCl_2.2H_2O$), from 2.31 g to 2.61 g of lactate, from 3.68 to 4.08 g of chloride (as NaCl, KCl and $CaCl_2.2H_2O$) and water in sufficient quantity to give 1000 ml solution.

The terms crystalloids and colloids in connection with fluid therapy are known in the art. They include plasma substitutes such as Haemaccel™ (polygecline based) and Gelofusine™ (gelatin based).

The invention will be further apparent from the following description of the figures and the associated figures.

The invention will be further understood by reference to the following specific description of the examples.

EXAMPLES

Methods

Dietary treatment

Female Sprague-Dawley rats (250–275 g) were fed standard laboratory chow (Agway PROLAB RMH 3000, Syracuse, N.Y.), chow and choline chloride (0.05–0.4%), chow and glycine (5%), or chow and 5% glycine and 0.4% choline chloride for 3 days. Rats were given free access to water and were maintained on a 12 h light/dark cycle.

Endotoxin treatment

After 3 days of feeding the rats the diets described above, LPS (*Escherichia coli* serotype 0111:b4; Sigma Chemical, St. Louis, Mo.) was suspended in pyrogen-free saline and injected into the tail vein. Survival was assessed after 24 h, and in some experiments, blood and tissue samples were collected 8 h after LPS injection. Serum was stored at −20° C. for measurement of total triglycerides and aspartate aminotransferase activity by standard enzymatic methods (Bergmeyer HU. Methods of Enzymatic Analysis. New York: Academic Press, 1988 and Bucolo G, David H. Quantitative determination of serum triglycerides by the use of enzymes. Clin. Chem. 1973; 19:476–482.). Liver and lung samples were fixed in phosphate-buffered eosin stained sections was performed.

TNF-α meeasurement

LPS (5 mg/kg) was injected via tail vein. After 1 h, blood samples were collected from the vena cava to determine circulating levels of TNF-α. To each 200 µl blood sample, 75 µl of aprotinin (Sigma) was added and TNF-α was measured by enzyme-linked immunosorbent assay (ELISA; Genzyme, Cambridge, Mass.). Livers were removed and immediately frozen in liquid nitrogen for measurement of TNF-α mRNA. Reverse transcriptase polymerase chain reaction and densitometry were used to quantify mRNA.

Kupffer cell isolation and culture

Kupffer cells were isolated from rats fed chow or choline-supplemented diets by collagenase digestion and differential centrifugation as described previously (Pertoft H. and Smedsrod B. Separation and characterization of liver cells. Pretlow II T G, Pretlow T P. Cell Separation: Methods and Selected Applications, Vol. 4, ed. Academic Press, 1987:1–24). Briefly, the portal vein was cannulated and livers were perfused with calcium and magnesium-free Hanks' balanced salt solution (HBSS; 37° C.) for 5 min. Perfusion was continued with HBSS containing 0.025% collagenase type IV (Sigma) for approximately 5 min. When digestion appeared complete, the liver was removed, placed in a beaker containing collagenase buffer and cut into small pieces. The suspension was filtered through nylon gauze and centrifuged for 10 min at 450× g at a temperature of 4° C. The cell pellet was resuspended in HBSS and parenchymal cells were removed by centrifugation at 50× g for 3 min. The nonparenchymal cell fraction was washed twice with buffer. Kupffer cells were isolated by centrifugation on a Percoll cushion at 1000 × g for 15 min. Viability was determined by trypan blue exclusion and was >90%. Cells were seeded on glass coveislips and culture medium was exchanged after 1 h to remove nonadherent cells. The culture medium used was Dulbecco's modified Eagle's medium (DMEM) supplemented with 10% fetal bovine serum, 100 U/ml penicillin G and 100 µg/ml streptomycin sulfate. Purity was determined from the percentage of cells that engulfed latex beads by phagocytosis and was found to be near 100%. Cells were cultured for approximately 24 h prior to experiments.

Measurement of $[Ca^{2+}]i$

The fluorescent $Ca^{2+}$ indicator dye fura-2 was used to measure intracellular $Ca^{2+}$ as detailed previously (Ikeijma K, Thurman R G. Glycine prevents elevation in intracellular $Ca^{2+}$ in Kupffer cells by endotoxin (LPS) via actions on a chloride channel. Hepatology 1995; 22:803). Briefly, Kupffer cells plated on coverslips were incubated in modified Hanks' buffer and 0.03% Pluronic F-127 (BASF Wyandotte, Wyandotte, Minn.) at room temperature for 1 h. Changes in fluorescence intensity of fura-2 at excitation (340 and 380 nm) and emission (520 nm) wavelengths was monitored in individual Kupffer cells and values were corrected for system noise and autofluorescence.

Statistical analysis

Results are represented as mean ±SE. Significance was determined using Student's t-test or Mann-Withney's rank-sum where appropriate. The Fisher exact test was used to determine significance in the mortality studies. $p<0.05$ was selected as the level of significance.

Results

Effect of choline on survival after LPS injection

Figure 1:
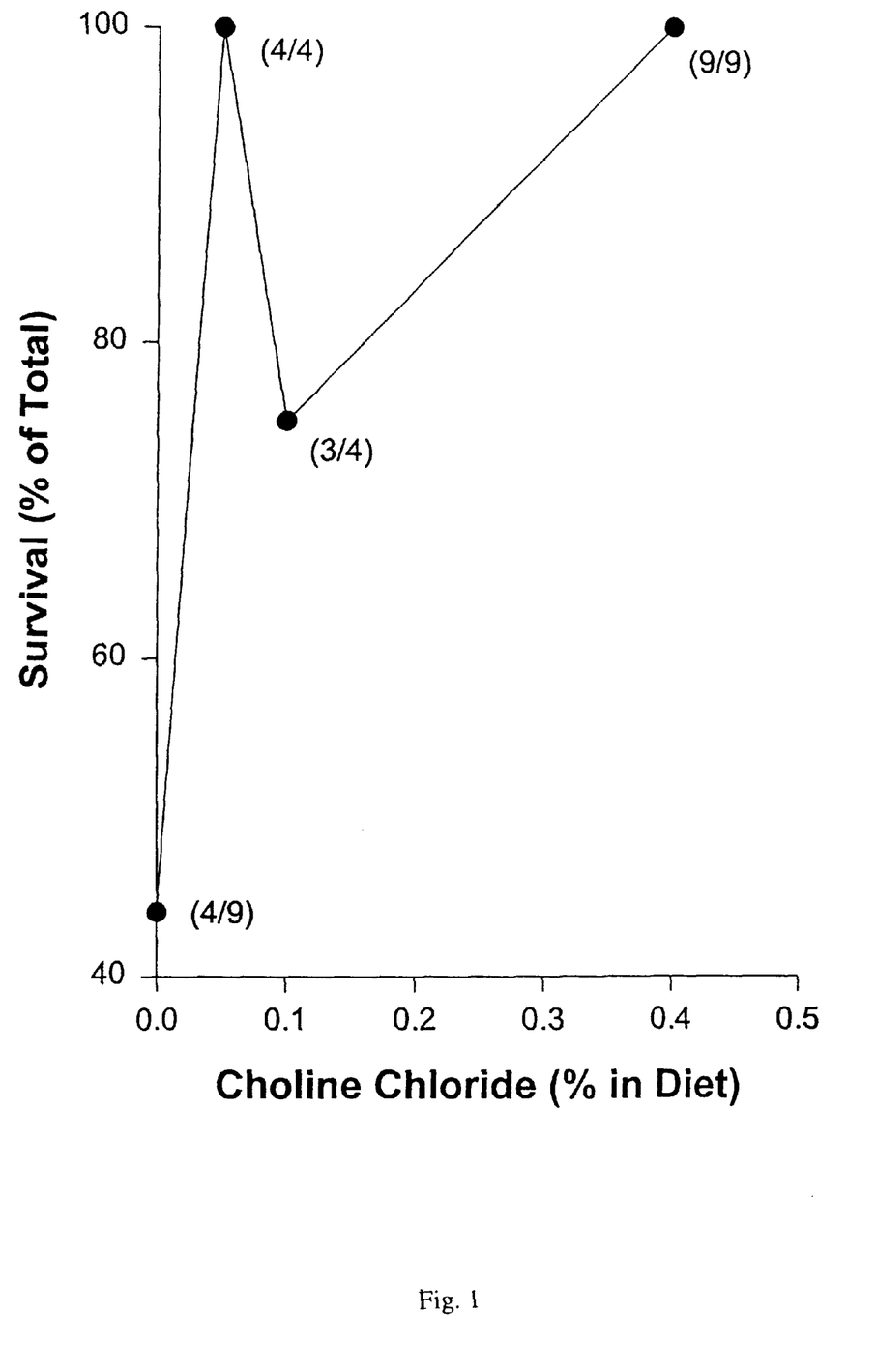
FIG. 1 shows the effect of choline on LPS-induced mortality. Rats were fed chow or chow+0.4% choline for 3 days. LPS was injected into the tail vein and mortality was assessed after 24 h. Fractions presented are survivors/total. *,p<0.05; Fisher's exact test.
Figure 2:
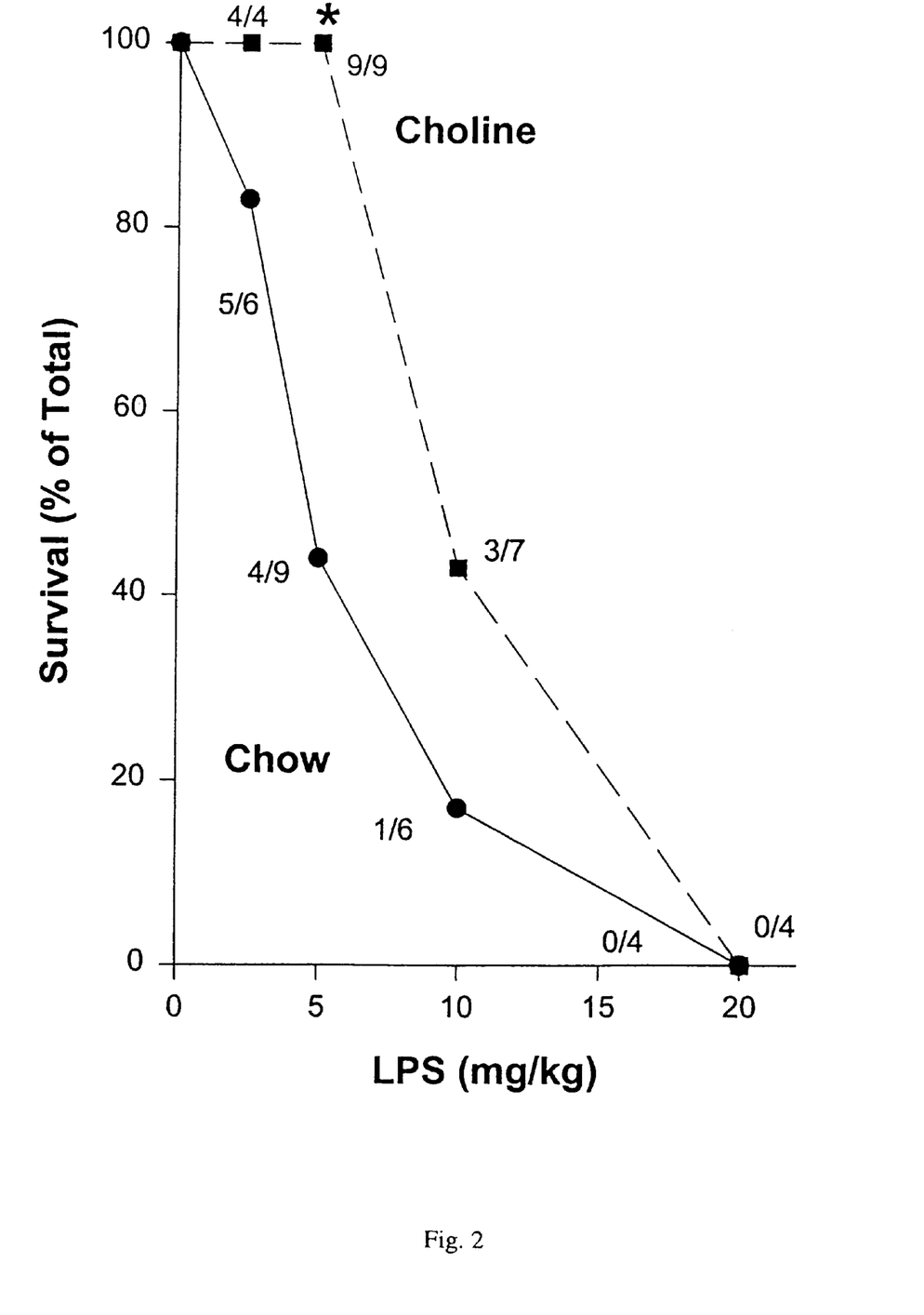
FIG. 2 shows dose-response of dietary choline on survival after LPS. Rats were fed chow with various amounts of added choline chloride for 3 days. LPS (5 mg/kg) was injected via the tail vein and survival was assessed after 24 h. Fractions represent survivors/total.

There were no significant differences in the average daily consumption or chow or choline-supplemented diets (18.1±1.3 and 18.5±1.3 g, respectively). Body weight for the two groups were also similar (chow 364±4 g; choline 365±3 g). After three days of feeding the rats specialized diets, LPS (2.5–20 mg/kg) was injected via the tail vein. Seventeen percent of rats fed chow died within 24 h following 2.5 mg/kg LPS, 56% died at the 5 mg/kg dose, 83% at 10 mg/kg, and 100% at 20 mg/kg (FIG. 1). Death usually occurred 8–12 h after LPS and surviving animals showed improvement after 24 h. The addition of 0.4% choline to the diet increased survival to 100% after injection of 2.5 or 5.0 mg/kg LPS (p<0.05) while 44% of rats survived at the 10 mg/kg dose (FIG. 1). Choline did not increase survival after 20 mg/kg LPS. The effect of increasing the amount of choline in the diet was also observed. Survival after a sublethal dose of LPS (5 mg/kg) increased from 17% (no addition) to 100% and 75% with the addition of 0.05% and 0.1% choline, respectively as shown in FIG. 2. Dietary supplementation with 0.4% choline significantly improved survival to 100% (p<0.05).

Glycine and choline are additive

In a previous study, dietary supplementation with glycine blunted Kupffer cell activation and increased survival due to endotoxin shock (Ikejima K, Iimuro Y, Forman D T, Thurman R G. A diet containing glycine improves survival in endotoxin shock in the rat. Am J Physiol 1996, 271:G97–103). Glycine most likely inhibits Kupffer cell activation due to LPS by hyperpolarization of the plasma membrane by activating a glycine-gated chloride channel. To determine if the effects of glycine and choline are additive, rats fed chow, chow supplemented with glycine or choline, or a combination of both were given LPS (10 mg/kg) as described above. Under these conditions 17% of chow-fed animals and 43% of choline-fed animals survived (Table 1). Glycine alone improved survival by 50%; however, given together, glycine and choline increased survival to 100%. Since the effects of glycine and choline are additive in this model, it is likely that choline acts at a site distinct from the choline channel affected by glycine.

TABLE 1

Effect of feeding diets containing glycine and choline on LPS-induced mortality

|  | Survivors/Total | % Survivors |
|---|---|---|
| No Addition | 1/6 | 17 |
| 0.4% Choline | 3/7 | 43 |
| 5% Glycine | 4/6 | 67 |
| 5% Glycine + 0.4% Choline | 6/6 | 100* |

Rats were fed a chow-based diet supplemented with 5% glycine or 0,4% choline chloride. Survival was assessed 24 h after injection of 10 mg/kg LPS as described above (n = 6).
*p < 0.05; Fisher's exact test.

Effect of choline on serum AST and histology after LPS

Figure 3:
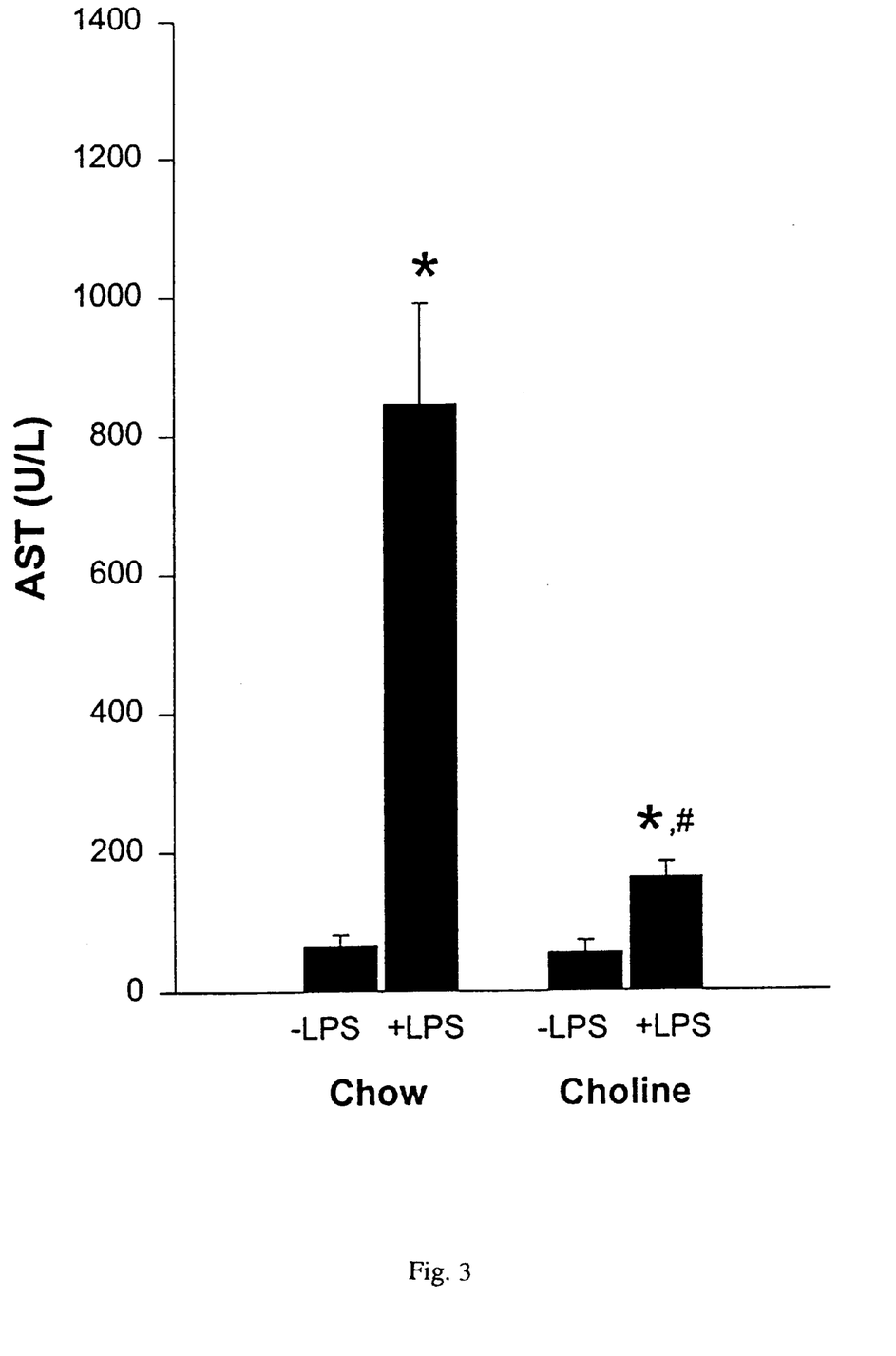
FIG. 3 shows the effect of choline on LPS-stimulated serum AST (aspartate aminotransferase). Conditions as in FIG. 1. Blood samples were collected 8 h after injection of 5 mg/kg LPS. *, p<0.05 compared to choline control, #, p<0.05 compared to chow+LPS by Mann-Whitney's rank-sum test; n=4.

Blood samples were collected 8 h after injection of 5 mg/kg LPS. Basal serum AST (aspartate aminotransferase) values were 65±33 U/l and 55±18 U/l in the chow and chow+0.4% choline groups, respectively (FIG. 3). Injection of LPS increased AST to 846±146 U/l in chow fed animals; however, this increase was significantly blunted by feeding choline with values only reaching 163±22 U/l (p<0.05); Mann-Whitney rank sum test). LPS induced massive necrosis and inflammation in livers from chow-fed rats. Pulmonary edema and marked increase in infiltrating inflammatory cells was also observed. Liver necrosis and pulmonary edema were both attenuated in choline-treated rats; choline significantly diminished liver and lung pathology scores.

Effect of choline on changes in $[Ca^{2+}]i$ in cultured Kupffer cells

Figure 4A:
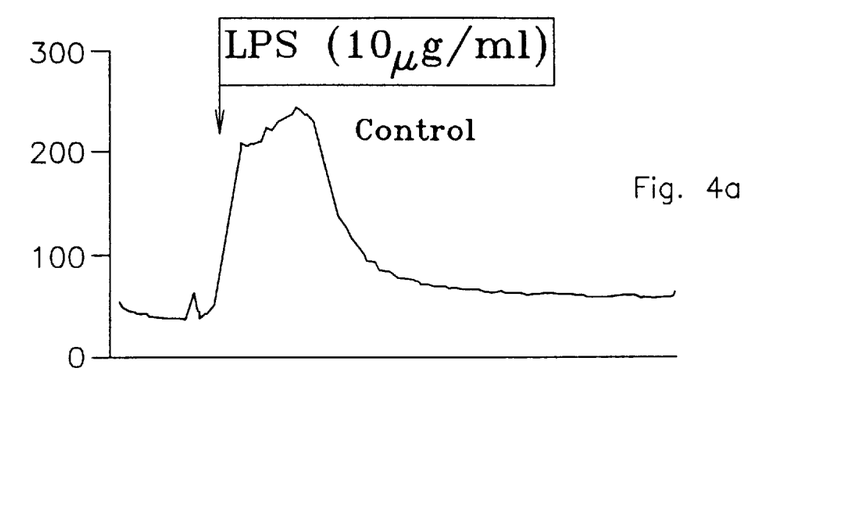
FIG. 4 shows the effect of choline on LPS-stimulated intracellular calcium levels in isolated Kupffer cell. $[Ca^{2+}]i$ in cultured Kupffer cells from chow FIG. 4A or chow+choline-fed rats FIG. 4B was measured fluorometrically using fura-2. Addition of LPS (10 µg/ml) is denoted with horizontal bars and arrows. Representative traces.
Figure 4B:
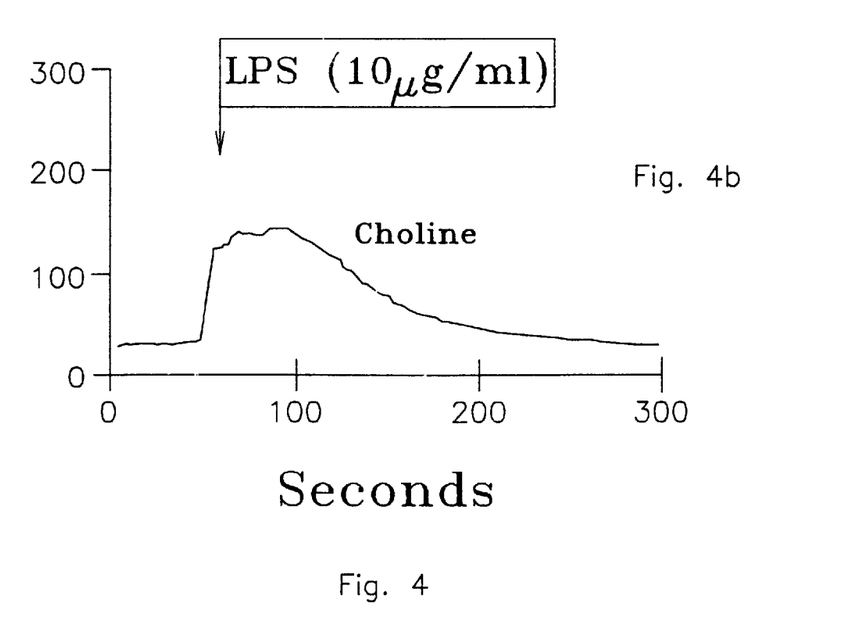
Figure 5:
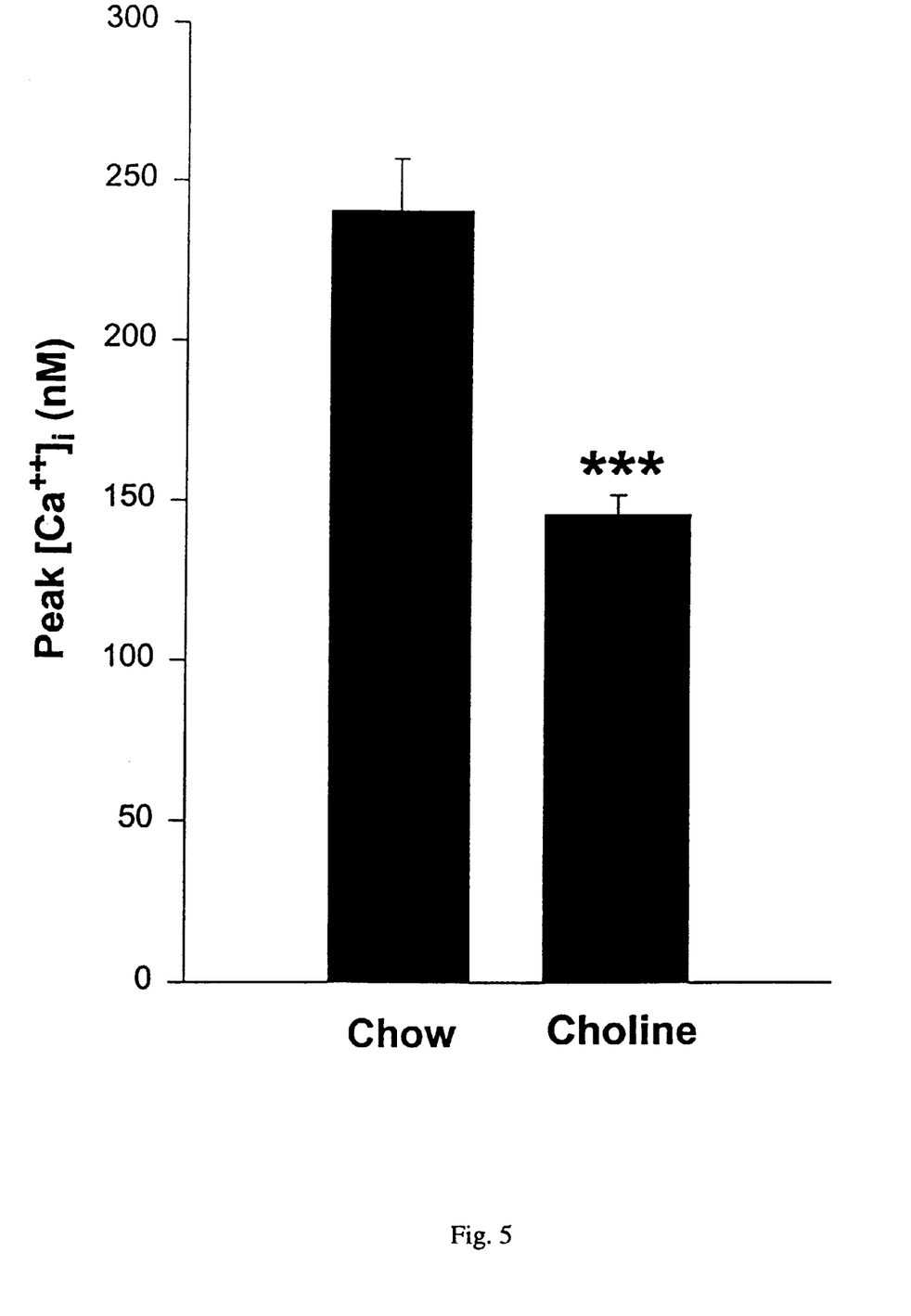
FIG. 5 shows the effect of choline on peak intracellular calcium levels following addition of LPS to isolated Kupffer cells. Conditions as in FIG. 4. Mean ± SEM of peak $[Ca^{2+}]i$ following LPS. ***, p<0.001 using student's t-test.
Figure 6:
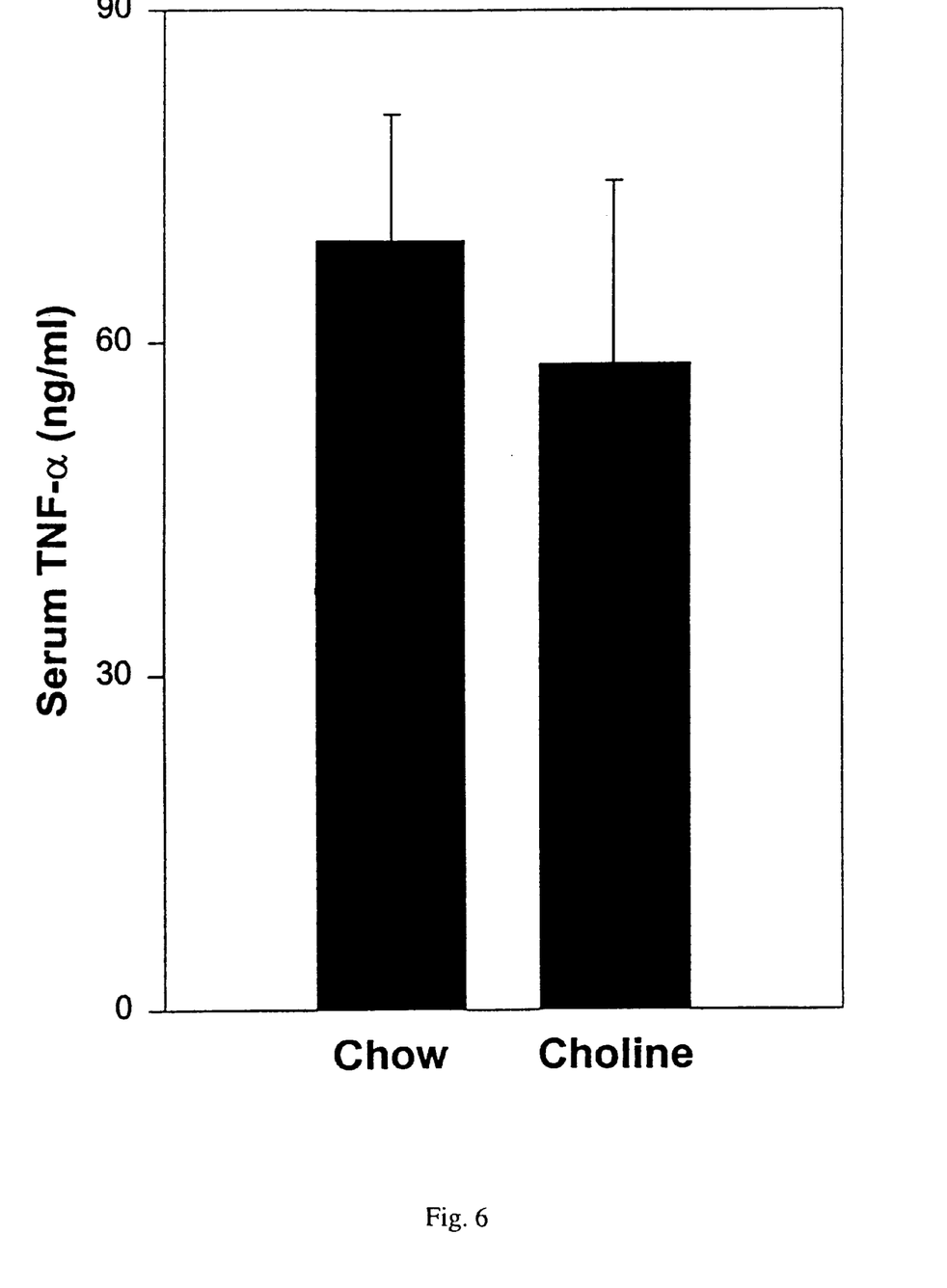
FIG. 6 shows the effect of choline on serum TNF-α levels after LPS injection. Blood samples were collected before and 1 h following injection of 5 mg/kg LPS. TNF-α was measured by enzyme-linked immunosorbent assay as detailed in METHODS. *, p<0.05 using student's t-test; n=6.
Figure 7:
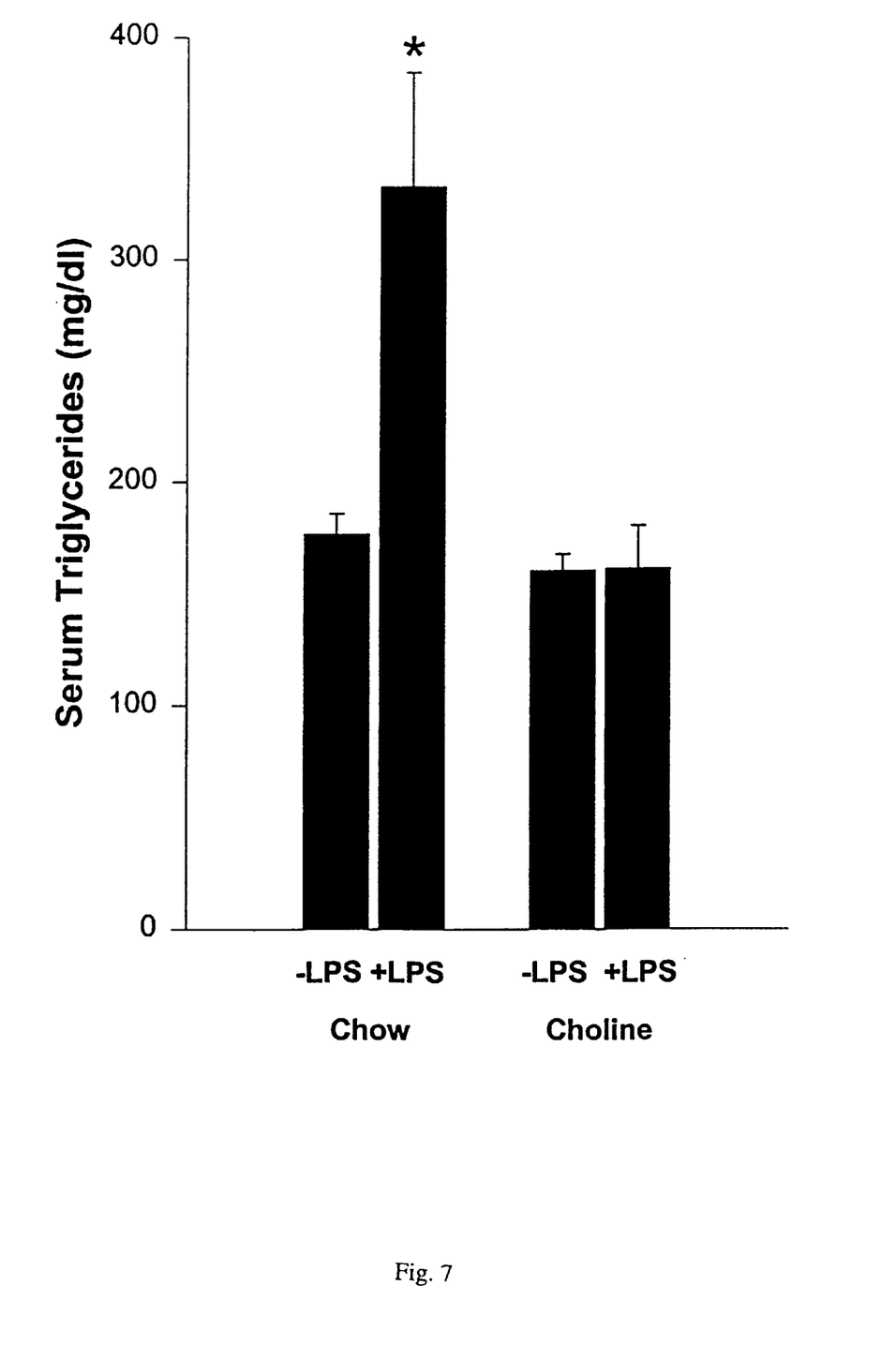
FIG. 7 shows the effect of choline on serum triglyceride levels. Blood samples were taken 8 h after LPS (5 mg/kg). Triglycerides were measured enzymatically in serum. *, p<0.05 by one-way analysis of variance; n=4.

Intracellular calcium was monitored fluorometrically in Kupffer cells isolated from chow or choline-fed animals (FIGS. 4 & 5). After the addition of 10 µg/ml LPS to the culture medium of Kupffer cells isolated from chow-red rats, $[Ca^{2+}]i$ rapidly increased reaching a peak value within 100 sec (241±17 nM; n=4), and declined to basal levels within 200 sec. The addition of 10 mM choline chloride to the culture medium 6 or 24 h prior to LPS did not affect increases in calcium caused by LPS (data not shown). However, when Kupffer cells were isolated from rats fed 0.4% choline for three days, the increase in $[Ca^{2+}]i$ due to LPS was only approximately 50% as large (FIGS. 4 & 5).

Effect of choline on serum TNF-α levels

Peak TNF-α release occurs approximately 1 h after injection of LPS. Therefore, in the present study serum TNF-α was measured 1 h after injection of 5 mg/kg LPS. There was an increase in serum TNF-α (69±6 ng/ml). The increase serum TNF-α was blunted by choline (58±8 ng/ml; p<0.08 by Student's t test). Endotoxin activates macrophages that, in turn, produce cytokines that mediate the host response to injury. TNF-α is believed to be responsible for the increases in triglyceride synthesis as well as increased production of VLDL during infection. Since protective effects of choline correlated with lower TNF-α production in response to LPS this indicated that the mechanism of choline protection most likely involves diminished macrophage activation.

Effect of choline on serum triglyceride levels

Gram-negative bacterial sepsis and endotoxin shock cause a disturbance in lipid metabolism that leads to hypertriglyceridemia, characterized by increased VLDL secretion. It has been shown that lipoproteins bind and detoxify endotoxin and treatment with lipoproteins such as VLDL protects against endotoxin-induced mortality. Therefore, the increase in lipoprotein production due to endotoxin may be a component of the defence mechanism against infection. Since choline is necessary for the synthesis of VLDL it was hypothesized by the present inventors that choline would increase survival by increasing circulating levels of very low density lipoprotein (VLDL), a lipoprotein that binds and detoxifies endotoxin. Since triglycerides compose 60% of VLDL, serum triglycerides were measured as a marker of VLDL. Prior to injection of LPS, serum triglyceride levels were within the normal range in chow and chow+ choline rats (177±9 and 160±7 mg/dl, respectively). Following LPS injection triglyceride levels increased to 333±51 mg/dl in chow-fed rats, an effect that was surprisingly blocked by choline (165±16 mg/dl) rather than enhanced. Therefore, it is unlikely that the mechanism of choline protection involves VLDL.

Enteral Compositions

In the following compositions MM stands for "mineral mixture", SM for "trace element mixture" and VM for "vitamin mixture". The composition of these three mixtures is as follows:

| Ingredients | g/100 g |
|---|---|
| MM | |
| Maltodextrins | 34.40 |
| Potassium citrate/phosphate | 34.60 |
| Magnesium dicitrate | 8.20 |
| Calcium chloride | 8.00 |
| Sodium citrate/chloride | 9.00 |
| Citric acid | 3.50 |
| Choline tartrate | 2.30 |
| SM | |
| Maltodextrins | 47.79 |
| Molybdenum-yeast | 18.00 |
| Chromium-yeast | 9.20 |
| Zinc sulfate | 7.00 |
| Selenium-yeast | 7.00 |
| Ferrum(II) sulfate | 6.92 |
| Copper(II) gluconate | 2.24 |
| Manganese(II) sulfate | 1.12 |
| Sodium fluoride | 0.70 |
| Potassium iodide | 0.03 |
| VM | |
| Maltodextrins | 43.44 |
| Sodium ascorbate | 35.00 |
| Vitamin E-Ac. 50% | 16.00 |
| Niacinamide | 1.55 |
| Vitamin A-Acetate | 1.20 |
| Ca-D-Panthothenate | 0.98 |
| Vitamin $K_1$ 1% | 0.71 |
| Vitamin $B_{12}$ 0.1% | 0.30 |

-continued

| Ingredients | g/100 g |
|---|---|
| Vitamin $D_3$ | 0.28 |
| Vitamin $B_6$ | 0.20 |
| Vitamin $B_1$ | 0.17 |
| Vitamin $B_2$ | 0.15 |
| Folic acid | 0.02 |
| Biotin | 0.01 |
| Composition Comprising Choline | |
| Water | 77.40 |
| Maltodextrins | 12.30 |
| Na/Ca caseinates | 4.60 |
| Choline tartrate | 0.80 |
| MM | 2.00 |
| SM | 0.05 |
| VM | 0.10 |
| β-Carotine | 0.03 |
| Lipids: | |
| Palm oil | 2.33 |
| Sunflower oil | 0.26 |
| Emulsifier Nathin E | 0.13 |
| | 100.00 |
| Composition Comprising Choline and Glycine | |
| Water | 77.40 |
| Maltodextrins | 9.30 |
| Na/Ca caseinates | 4.60 |
| Choline tartrate | 0.80 |
| Glycine | 3.00 |
| MM | 2.00 |
| SM | 0.05 |
| VM | 0.10 |
| β-Carotine | 0.03 |
| Lipids: | |
| Palm oil | 2.36 |
| Sunflower oil | 0.23 |
| Emulsifier Nathin E | 0.13 |
| | 100.00 |
| Composition Comprising Choline and Fish Oil (ω-3 fatty acids) | |
| Water | 77.40 |
| Maltodextrins | 12.30 |
| Na/Ca caseinates | 4.60 |
| Choline tartrate | 0.80 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |
| | 100.00 |
| Composition Comprising Choline and Arginine | |
| Water | 77.40 |
| Maltodextrins | 11.13 |
| Na/Ca caseinates | 4.60 |
| Choline tartrate | 0.80 |
| Arginine | 1.17 |
| MM | 2.00 |
| SM | 0.05 |
| VM | 0.10 |
| β-Carotine | 0.03 |
| Palm oil | 2.33 |
| Sunflower oil | 0.26 |
| Emulsifier Nathin E | 0.13 |
| | 100.00 |

-continued

| Ingredients | g/100 g |
|---|---|
| Composition Comprising Choline, Glycine and Fish Oil (ω-3 fatty acids) | |
| Water | 77.40 |
| Maltodextrins | 9.30 |
| Na/Ca caseinates | 4.60 |
| Choline tartrate | 0.80 |
| Glycine | 3.00 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |
| | 100.00 |
| Composition Comprising Choline, Glycine and Arginine | |
| Water | 77.40 |
| Maltodextrins | 8.13 |
| Na/Ca caseinates | 4.60 |
| Choline tartrate | 0.80 |
| Glycine | 3.00 |
| Arginine | 1.17 |
| MM | 2.00 |
| SM | 0.05 |
| VM | 0.10 |
| β-Carotine | 0.03 |
| Lipids: | |
| Palm oil | 2.33 |
| Sunflower oil | 0.26 |
| Emulsifier Nathin E | 0.13 |
| | 100.00 |
| Composition Comprising Choline, Glycine, Arginine and Fish Oil (ω-3 fatty acids) | |
| Water | 77.40 |
| Maltodextrins | 8.15 |
| Na/Ca caseinates | 4.60 |
| Choline tartrate | 0.80 |
| Glycine | 3.00 |
| Arginine | 1.17 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |

-continued

| Ingredients | g/100 g |
|---|---|
| | 100.00 |
| Composition Comprising Choline, Glycine, Arginine, RNA and Fish Oil (ω-3 fatty acids) | |
| Water | 77.40 |
| Maltodextrins | 8.02 |
| Na/Ca caseinates | 4.60 |
| Choline tartrate | 0.80 |
| Glycine | 3.00 |
| Arginine | 1.17 |
| Yeast extract RNA | 0.14 |
| MM | 2.00 |
| SM | 0.05 |
| VM | 0.10 |
| β-Carotine | 0.03 |
| Lipids: | |
| Palm oil | 1.32 |
| Sunflower oil | 0.23 |
| Emulsifier Nathin E | 0.13 |
| Fish Oil EPAX 3000 TG | 1.04 |
| | 100.00 |

As already set out above, fish oil is a natural source for omega-3 PUFAs whereas sunflower oil is a natural source for omega-6 PUFAs.

We claim:

1. A method for the treatment of endotoxic shock comprising enterally administering to a human or other mammal in need of such a treatment an effective amount of choline for reducing endotoxin-induced injury or mortality, or both.

2. The method according to claim 1 wherein from 1.5 to 20 grams of choline are administered daily.

3. A method for the treatment of endotoxic shock comprising enterally administering to a human or other mammal in need of such a treatment a combined amount of choline and glycine effective for reducing endotoxin-induced injury or mortality, or both.

4. The method of claim 3 wherein from 1.5 to 20 grams of choline and from 1.5 to 75 grams of glycine are administered daily.

5. A method for the treatment of endotoxin-related injury comprising enterally administering to a human or other mammal in need of such a treatment an effective amount of choline to reduce the endotoxin-related injury.

6. The method of claim 5 wherein the endotoxin-related injury is alcohol-induced liver injury.

* * * * *

UNITED STATES PATENT AND TRADEMARK OFFICE
CERTIFICATE OF CORRECTION

PATENT NO. : 6,013,273
DATED : January 11, 2000
INVENTOR(S) : Schneider

It is certified that error appears in the above-identified patent and that said Letters Patent is hereby corrected as shown below:

<u>Title page,</u>
Item [75] should read as follows:
-- APPLICANT(S)    HEINZ SCHNEIDER, CORDAST SWITZERLAND --

Signed and Sealed this

Twenty-fifth Day of December, 2001

Attest:

JAMES E. ROGAN
*Attesting Officer*    *Director of the United States Patent and Trademark Office*